United States Patent [19]
Weber et al.

[11] Patent Number: 4,839,282
[45] Date of Patent: Jun. 13, 1989

[54] PREPARATION OF 3-OXO-$\Delta^{1,4}$-STEROIDS
[75] Inventors: Alfred Weber; Mario Kennecke, both of Berlin, Fed. Rep. of Germany
[73] Assignee: Schering Aktiengesellschaft, Berlin and Bergkamen, Fed. Rep. of Germany
[21] Appl. No.: 809,810
[22] Filed: Dec. 17, 1985

Related U.S. Application Data

[63] Continuation of Ser. No. 561,510, Dec. 15, 1983, abandoned, which is a continuation of Ser. No. 334,045, Dec. 23, 1981, abandoned.

[30] Foreign Application Priority Data

Dec. 23, 1980 [DE] Fed. Rep. of Germany ....... 3049399

[51] Int. Cl.$^4$ .......................... C12P 33/02; C12P 33/16
[52] U.S. Cl. ......................................... 435/61; 435/55
[58] Field of Search ..................................... 435/61, 55
[56] References Cited

U.S. PATENT DOCUMENTS 3,388,042 6/1968 Arima et al. ........................ 435/61
4,101,378 7/1978 Nishikawa et al. .................. 435/61
4,431,732 2/1984 Weber et al. ......................... 435/61

Primary Examiner—Alvin E. Tanenholtz
Attorney, Agent, or Firm—Millen & White

[57] ABSTRACT

A process for preparing a 3-oxo-$\Delta^{1,4}$-steroid comprises fermenting the corresponding 3-oxo-$\Delta^4$-steroid, saturated in the 1,2-position, with a living culture of *Arthrobacter simplex* in the presence of 0.04 g to 0.12 g of cobalt(II) ions per liter of culture broth.

6 Claims, No Drawings

PREPARATION OF 3-OXO-$\Delta^{1,4}$-STEROIDS

This is a continuation of application Ser. No. 561,510 filed Dec. 15, 1983 now abandoned, which is a continuation of Ser. No. 334,045, filed Dec. 23, 1981, now abandoned.

BACKGROUND OF THE INVENTION

Fermentations of 3-oxo-$\Delta^4$-steroids with living cultures of known steroid-$\Delta^1$-dehydrogenating microorganisms, such as *Bacillus lentus* ATCC 13 805, *Bacillus sphaericus* ATCC 7054, ATCC 7055, and ATCC 12 488, *Bacillus subtilus* NRRL B 558, *Arthrobacter simplex*, as well as *Norcardia corallina* ATCC 4273 and 4275 frequently produce unsatisfactory results, in part because the conversion rate is two low or no adequate conversion of the substrate is observed, and in part because the substrate is greatly metabolized.

SUMMARY OF THE INVENTION

It is an object of this invention to provide a new fermentative dehydrogenation process.

Upon further study of the specification and appended claims, further objects and advantages of this invention will become apparent to those skilled in the art.

It has now been found that the microbiological $\Delta^1$-dehydrogenation of 3-oxo-$\Delta^4$-steroids can be conducted with satisfactory results by using, for the dehydrogenation of such substrates, a microorganism of the species *Arthrobacter simplex* and by conducting the reaction in the presence of 0.04–0.12 g, preferably 0.04–0.08 g, of cobalt(II) ions per liter of culture. Suitable *Arthrobacter simplex* strains include, for example, the strains IFO (3530), ATCC 13 260, and especially ATCC 6946.

DETAILED DISCUSSION

It has long been known that *Arthrobacter simplex*—previously named *Corynebacterium simplex*—is active for $\Delta^1$-dehydrogenation of steroids. This microorganism is frequently used in technical applications in industry, since it has the advantage over most of the other aforementioned steroid-$\Delta^1$-dehydrogenating microorganisms that its reaction proceeds substantially faster than those of the other microorganisms; however, on the other hand, *Arthrobacter simplex* also has two disadvantages. The microorganism frequently tends to metabolize steroids during a prolonged fermentation period, leading to not inconsiderable losses in yield of the desired product. Moreover, it frequently tends to stop the reaction when there is still 1–3% of starting steroid remaining in the culture broth. This makes it often quite difficult to obtain the products of the process in a purity indispensable for pharmaceuticals.

These disadvantages can be avoided by conducting the $\Delta^1$-dehydrogenation with *Arthrobacter simplex* in the presence of 0.04 g to 0.12 g of cobalt(II) ions per liter of culture broth. A smaller concentration of cobalt ions does not provide any appreciable effect; a higher concentration of cobalt(II) ions has an inhibitory effect. Suitable cobalt(II)-ion-yielding agents include water-soluble cobalt salts, e.g. $CoCl_2$, $Co(NO_3)_2$, $CoSO_4$, or $CoSO_4.7H_2O$. The anions of these salts are not critical for the operability of the process, since the cobalt(II) salts are dissociated in the culture medium.

Otherwise, the process of this invention is conducted under conventional conditions customarily employed for the $\Delta^1$-dehydrogenation of steroids using microorganisms of the species *Arthrobacter simplex* formerly named *Cornebacterium simplex* (see e.g. W. Charney and H. L. Herzog: Microbial Transformations of Steroids Academic Press, New York, 1967, pages 356 ff) whose disclosure are incorporated by reference herein.

Under the culturing conditions usually employed for this microorganism, a submerged culture is grown in a suitable nutrient medium with aeration. Then, the substrate (dissolved in a suitable solvent or preferably in emulsified form) is added to the culture and the mixture is fermented until maximum substrate conversion has been obtained.

Suitable substrate solvents include, for example, methanol, ethanol, glycol monomethyl ether, dimethylformamide, dimethyl sulfoxide, or hexamethylphosphoric triamide. Emulsification of the substrate can be achieved, for example, by introducing it in micronized form or dissolved in a water-miscible solvent (such as methanol, ethanol, acetone, glycol monomethyl ether, dimethylformamide, or dimethyl sulfoxide) through nozzles under strong turbulence into (preferably demineralized) water containing the usual emulsifiers. Suitable emulsifiers include nonionic emulsifiers, such as ethylene oxide adducts or fatty acid esters of polyglycol. Examples of suitable emulsifiers include the commercial surfactants "Tegin", "Tagat", "Tween", and "Span".

The optimum substrate concentration, timing of addition of the substrate, and duration of fermentation are dependent on the type of microorganism employed. These variables are determined in each individual case, as generally required in microbiological steroid conversions, by routine preliminary experiments as known to those skilled in the art.

As one example of the applicability of this invention, there can be mentioned a process for the preparation of a 3-oxo-$\Delta^{1,4}$-steroid of the formula

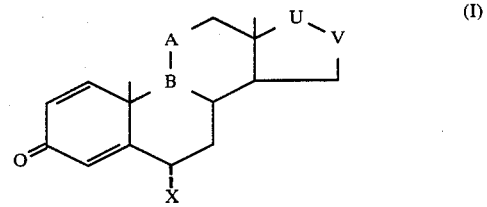

wherein X is hydrogen, chlorine, fluorine or methyl,

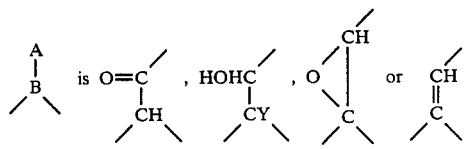

Y is hydrogen, fluorine, or chlorine, and

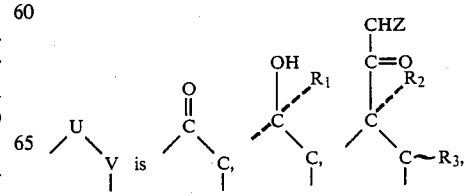

-continued

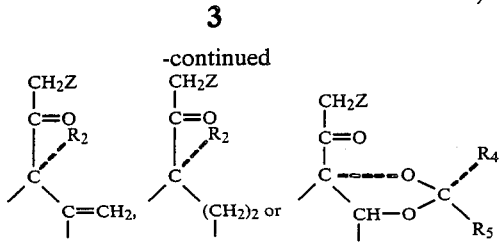

wherein

Z is hydrogen, hydroxy, fluorine, or chlorine, $R_1$ is hydrogen or an alicyclic hydrocarbon residue of 1-4 carbon atoms, $R_2$ is hydrogen, hydroxy, alkyl of 1-6 carbon atoms optionally interrupted by an oxygen atom or a sulfur atom, alkanoyloxy of 1-6 carbon atoms, or benzoyloxy, $R_3$ is hydrogen, hydroxy or methyl, and $R_4$ and $R_5$ each independently is alkyl of 1-4 carbon atoms, comprising fermenting a corresponding 3-oxo-$\Delta^4$-steroid of formula (II)

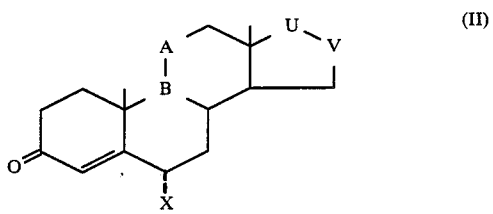

wherein X,

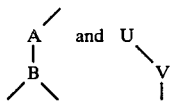

are as defined above, or a 21-ester thereof with an alkanecarboxylic acid of 1-6 carbon atoms.

The 3-oxo-$\Delta^{1,4}$-steroids preparable by the process of this invention are all well known to be active as antiinflammatories The compounds of formula (I) are similarly active. Moreover, these compounds can be conventionally used as intermediates in the preparation of other well known useful steroids.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) A 2-liter Erlenmeyer flask charged with 1 liter of a sterile nutrient solution containing 0.5% cornsteep liquor
0.05% glucose monohydrate
0.1% yeast extract
adjusted to pH 7.0 is inoculated with a supernatant broth of a dry culture of *Arthrobacter simplex* ATCC 6946 and shaken at 30° C. for 72 hours at 180 rpm.

(b) A 50-liter fermentor with 30 l of sterile nutrient solution containing 0.5% cornsteep liquor
0.05% a glucose monohydrate
0.1% yeast extract
4 ml silicone SH
4 ml "Pluronic"
adjusted to pH 7.0 is inoculated with 1 liter of *Arthrobacter simplex* incubation culture, and this preliminary culture is incubated at 30° C. under aeration (2 m³ per hour) and agitation (220 rpm) for 24 hours.

(c) 7.5 g of 9$\beta$,11$\beta$-epoxy-17$\alpha$-hydroxy-16$\beta$-methyl-4-pregnene-3,20-dione is dissolved in 300 ml of ethylene glycol monomethyl ether and thereafter filtered under sterile conditions.

(d) 12 g of $CoSO_4.7H_2O$ and 12 g of $(NH_4)_2SO_4$ are dissolved in 500 ml of water, adjusted to pH 6.5, and sterilized.

(e) A 50-liter fermentor is charged with 30 l of a sterile nutrient solution containing 0.5% cornsteep liquor
0.05% glucose monohydrate
0.3% a "protein hydrolysate"
4 ml silicone SH
4 ml "Pluronic"
adjusted to pH 7.0 inoculated with 3 l of *Arthrobacter simplex* preliminary culture, and incubated under aeration (2 m³ per hour) and agitation (220 rpm) for 6 hours at 30° C. Then the sterile 9$\beta$,11$\beta$-epoxy-17$\alpha$-hydroxy-16$\beta$-methyl-4-pregnene-3,20-dione solution prepared in paragraph (c) and the additives produced in paragraph (d) are added thereto. The fermentation is then continued for another 20 hours.

After fermentation has been completed, the culture broth, stabilized with 5 l of ethylene chloride, is extracted three times with respectively 20 l of ethylene chloride, and the ethylene chloride extract is concentrated in a forced circulation evaporator at maximally 50° C. under vacuum. Thereafter the product is purified by chromatography on aluminum oxide.

Yield: 5.8 g of 9$\beta$,11$\beta$-epoxy-17$\alpha$-hydroxy-16$\beta$-methyl-1,4-pregnadiene-3,20-dione, mp 212/213°-214° C.

EXAMPLE 2

(a) A 2-liter Erlenmeyer flask charged with 1 liter of a sterile nutrient solution containing 0.5% cornsteep liquor
0.05% glucose monohydrate
0.1% yeast extract
adjusted to pH 7.0 is inoculated with a supernatant broth of a dry culture of *Arthrobacter simplex* ATCC 6946 and shaken at 30° C. for 72 hours at 180 rpm.

(b) A 50-liter fermentor with 30 l of sterile nutrient solution containing 0.5% cornsteep liquor
0.05% glucose monohydrate
0.1% yeast extract
4 ml silicone SH
4 ml "Pluronic"
adjusted to pH 7.0 is inoculated with 1 liter of *Arthrobacter simplex* incubation culture, and this preliminary culture is incubated at 30° C. under aeration (2 m³ per hour) and agitation (220 rpm) for 24 hours.

(c) 7.5 g of 17α-hydroxy-16β-methyl-4,9(11)pregnadiene-3,20-dione is dissolved in 150 ml of ethylene glycol monomethyl ether at 60° C. and then filtered under sterile conditions.

(d) 18 g of $CoSO_4.7H_2O$ and 18 g of $(NH_4)_2SO_4$ are dissolved in 500 ml of water, adjusted to pH 6.5, and sterilized.

(e) A 50-liter fermentor is charged with 30 l of a sterile nutrient solution containing
0.5% cornsteep liquor
0.05% glucose monohydrate
0.3% "protein hydrolysate"
4 ml silicone SH
4 ml "Pluronic"
adjusted to pH 7.0
inoculated with 3 l of *Arthrobacter simplex* preliminary culture, and incubated under aeration (2 m³ per hour) and agitation (220 rpm) for 6 hours at 30° C. Then the sterile 17α-hydroxy-16β-methyl-4,9(11)-pregnadiene-3,20-dione solution produced in paragraph (c) and the additives prepared in paragraph (d) are added thereto. Fermentation is then continued for 24 hours.

After fermentation has been accomplished, the culture broth, stabilized with 5 l of ethylene chloride, is extracted three times with respectively 20 l of ethylene chloride, and the ethylene chloride extract is concentrated under vacuum in a forced circulation evaporator at maximally 50° C. The product is thereafter purified by chromatography on aluminum oxide.

Yield: 6.2 g of 17α-hydroxy-16β-methyl-1,4,9(11)pregnatriene-3,20-dione, mp 177°–178° C.

EXAMPLE 3

(a) A 2-liter Erlenmeyer flask charged with 1 liter of a sterile nutrient solution containing
0.5% cornsteep liquor
0.05% glucose monohydrate
0.1% yeast extract
adjusted to pH 7.0
is inoculated with a supernatant broth of a dry culture of *Arthrobacter simplex* ATCC 6946 and shaken at 30° C. for 72 hours at 180 rpm.

(b) A 30-liter fermentor with 20 l of a sterile nutrient solution containing
0.5% cornsteep liquor
0.05% glucose monohydrate
0.1% yeast extract
4 ml silicone SH
4 ml "Pluronic"
adjusted to pH 7.0
is inoculated with 1 liter of *Arthrobacter simplex* incubation culture, and this preliminary culture is incubated at 30° C. under aeration (2 m³ per hour) and agitation (220 rpm) for 24 hours.

(c) 6 g of 17α,21-dihydroxy-16-methylene-4-pregnene-3,11,20-trione is dissolved in 300 ml of hexamethylphosphoric triamide and thereafter filtered under sterile conditions.

(d) 9 g of $CoSO_4.7H_2O$ and 9 g of $(NH_4)_2SO_4$ are dissolved in 500 ml of water, adjusted to pH 6.5, and sterilized.

(e) A 30-liter fermentor is charged with 20 l of a sterile nutrient solution containing
0.5% cornsteep liquor
0.05% glucose monohydrate
0.3% "protein hydrolysate"
4 ml silicone SH
4 ml "Pluronic"
adjusted to pH 7.0
inoculated with 1.5 l of *Arthrobacter simplex* preliminary culture, and incubated under aeration (2 m³ per hour) and agitation (220 rpm) for 6 hours at 30° C. Then the sterile 21-acetoxy-17α-hydroxy-16-methylene-4-pregnene-3,11,20-trione solution produced in paragraph (c) and the additives produced in paragraph (d) are added to the culture. Thereafter, fermentation is continued for 16 hours.

After fermentation has been completed, the culture broth, stabilized with 3 l of ethylene chloride, is extracted three times with respectively 10 l of ethylene chloride, and the ethylene chloride extract is concentrated under vacuum in a forced circulation evaporator at maximally 50° C. The product is then purified by chromatography on aluminum oxide.

Yield: 4.5 g of 17α,21-dihydroxy-16-methylene-1,4-pregnadiene-3,11,20-trione, mp 218°–219° C.

EXAMPLE 4

(a) A 2-liter Erlenmeyer flask charged with 1 liter of a sterile nutrient solution containing
0.5% cornsteep liquor
0.05% glucose monohydrate
0.1% yeast extract
adjusted to pH 7.0
is inoculated with a supernatant broth of a dry culture of *Arthrobacter simplex* ATCC 6946 and shaken at 30° C. for 72 hours at 180 rpm.

(b) A 30-liter fermentor with 20 l of a sterile nutrient solution containing
0.5% cornsteep liquor
0.05% glucose monohydrate
0.1% yeast extract
4 ml silicone SH
4 ml "Pluronic"
adjusted to pH 7.0
is inoculated with 1 liter of *Arthrobacter simplex* incubation culture, and this preliminary culture is incubated at 30° C. under aeration (2 m³ per hour) and agitation (220 rpm) for 24 hours.

(c) 6.0 g of 11β,17aα,21-trihydroxy-D-bromo-4-pegnene-3,20-dione is dissolved in 150 ml of hexamethylphosphoric triamide and then filtered under sterile conditions.

(d) 9 g of $CoSO_4.7H_2O$ and 9 g of $(NH_4)_2SO_4$ are dissolved in 400 ml of water, adjusted to pH 6.5, and sterilized.

(e) A 30-liter fermentor is charged with 20 l of a sterile nutrient solution containing
0.5% cornsteep liquor
0.05% glucose monohydrate
0.3% "protein hydrolysate"
4 ml silicone SH
4 ml "Pluronic"
adjusted to pH 7.0
inoculated with 1.5 l of *Arthrobacter simplex* preliminary culture, and incubated under aeration (2 m³ per hour) and agitation (220 rpm) for 6 hours at 30° C. The sterile 11β,17aα,21-trihydroxy-D-homo-4-pregnene-3,20-dione solution produced in paragraph (c) and the additives produced in paragraph (d) are then added to the culture. Fermentation is subsequently continued for 18 hours.

After fermentation has taken place, the culture broth, stabilized with 3 l of ethylene chloride, is extracted three times with respectively 15 ml of ethylene chloride, and the ethylene chloride extract is concentrated under vacuum in a forced circulation evaporator at maximally 50° C. The product is then purified by chromatography on aluminum oxide.

Yield: 5.0 g of 11β,17aα,21-trihydroxy-D-homo-1,4-pregnadiene-3,20-dione, mp 248°–249° C. (decomposition).

EXAMPLE 5

(a) A 2-liter Erlenmeyer flask charged with 1 liter of a sterile nutrient solution containing
0.5% cornsteep liquor
0.05% glucose monohydrate
0.1% yeast extract
adjusted to pH 7.0
is inoculated with a supernatant broth of a dry culture of *Arthrobacter simplex* ATCC 6946 and shaken at 30° C. for 72 hours at 180 rpm.

(b) A 50-liter fermentor with 30 l of a sterile nutrient solution containing
0.5% cornsteep liquor
0.05% glucose monohydrate
0.1% yeast extract
4 ml silicone SH
4 ml "Pluronic"
adjusted to pH 7.0
is inoculated with 1 liter of *Arthrobacter simplex* incubation culture, and this preliminary culture is incubated at 30° C. under aeration (2 m³ per hour) and agitation (200 rpm) for 24 hours.

(c) 15 g of 6α-fluoro-11β,21-dihydroxy-16α-methyl-4-pregnene-3,20-dione is dissolved in 300 ml of hexamethylphosphoric triamide and thereafter filtered under sterile conditions.

(d) 12 g of CoSO$_4$.7H$_2$O and 12 g of (NH$_4$)$_2$SO$_4$ are dissolved in 500 ml of water, adjusted to pH 6.5, and sterilized.

(e) A 50-liter fermentor is charged with 30 l of a sterile nutrient solution containing
0.5% cornsteep liquor
0.05% glucose monohydrate
0.3% "protein hydrolysate"
4 ml silicone SH
4 ml "Pluronic"
adjusted to pH 7.0
inoculated with 3 l of *Arthrobacter simplex* preliminary culture, and incubated under aeration (2 m³ per hour) and agitation (220 rpm) for 6 hours at 30° C. Then, the sterile 6α-fluoro-11β,21-dihydroxy-16α-methyl-4-pregnene-3,20-dione solution produced in paragraph (c) and the additives prepared in paragraph (d) are added to the culture. The fermentation is thereafter continued for 22 hours.

After fermentation is complete, the culture broth, stabilized with 5 l of ethylene chloride, is extracted three times with respectively 20 l of ethylene chloride, and the ethylene chloride extract is concentrated under vacuum in a forced circulation evaporator at maximally 50° C. Then the product is purified by chromatography on aluminum oxide.

Yield: 13.1 g of 6α-fluoro-11β,21-dihydroxy-16α-methyl-1,4-pregnadiene-3,20-dione, mp 180/181°–182° C.

EXAMPLE 6

(a) A 2-liter Erlenmeyer flask charged with 1 liter of a sterile nutrient solution containing
0.5% cornsteep liquor
0.05% glucose monohydrate
0.1% yeast extract
adjusted to pH 7.0
is inoculated with a supernatant broth of a dry culture of *Arthrobacter simplex* ATCC 6946 and shaken at 30° C. for 72 hours at 180 rpm.

(b) A 50-liter fermentor with 30 l of a sterile nutrient solution containing
0.5% cornsteep liquor
0.05% glucose monohydrate
0.1% yeast extract
4 ml silicone SH
4 ml "Pluronic"
adjusted to pH 7.0
is inoculated with 1 liter of *Arthrobacter simplex* incubation culture, and this preliminary culture is incubated at 30° C. under aeration (2 m³ per hour) and agitation (220 rpm) for 24 hours.

(c) 15 g of 11β,21-dihydroxy-16α,17α-isopropylidenedioxy-4-pregnene-3,20-dione is dissolved in 300 ml of ethylene glycol monomethyl ether and subsequently filtered under sterile conditions.

(d) 12 g of CoSO$_4$.7H$_2$O and 12 g of (NH$_4$)$_2$SO$_4$ are dissolved in 500 ml of water, adjusted to pH 6.5, and sterilized.

(e) A 50-liter fermentor is charged with 30 l of a sterile nutrient solution containing
0.5% cornsteep liquor
0.05% glucose monohydrate
0.3% "protein hydrolysate"
4 ml silicone SH
4 ml "Pluronic"
adjusted to pH 7.0
inoculated with 3 l of *Arthrobacter simplex* preliminary culture, and incubated under aeration (2 m³ per hour) and agitation (220 rpm) for 6 hours at 30° C. The sterile solution of 11β,21-dihydroxy-16α,17α-isopropylidenedioxy-4-pregnene-3,20-dione prepared in paragraph in paragraph (c) and the additives produced in paragraph (d) are then added to the culture. Fermentation is thereafter continued for 20 hours.

After fermentation has been accomplished, the culture broth, stabilized with 5 l of ethylene chloride, is extracted three times with respectively 20 l of ethylene chloride, and the ethylene chloride extract is concentrated under vacuum in a forced circulation evaporator at maximally 50° C. Thereafter the product is purified by chromatography on aluminum oxide.

Yield: 13.6 g of 11β,21-dihydroxy-16α,17α-isopropylidenedioxy-1,4-pregnadiene-3,20-dione, mp 241°–242.5° C.

EXAMPLE 7

(a) A 2-liter Erlenmeyer flask charged with 1 liter of a sterile nutrient solution containing
0.5% cornsteep liquor
0.05% glucose monohydrate
0.1% yeast extract
adjusted to pH 7.0
is inoculated with a supernatant broth of a dry culture of *Arthrobacter simplex* ATCC 6946 and shaken at 30° C. for 72 hours at 180 rpm.

(b) A 50-liter fermentor with 30 l of a sterile nutrient solution containing
0.5% cornsteep liquor
0.05% glucose monohydrate
0.1% yeast extract 4 ml silicone SH
4 ml "Pluronic"
adjusted to pH 7.0
is inoculated with 1 liter of *Arthrobacter simplex* incubation culture, and this preliminary culture is incubated at 30° C. under aeration (2 m$^3$ per hour) and agitation (220 rpm) for 24 hours.

(c) 21 g of 11β,17α,21-trihydroxy-6α-methyl-4-pregnene-3,20-dione is dissolved in 300 ml of ethylene glycol monomethyl ether and then filtered under sterile conditions.

(d) 12 g of CoSO$_4$.7H$_2$O and 12 g of (NH$_4$)$_2$SO$_4$ are dissolved in 500 ml of water, adjusted to pH 6.5, and sterilized.

(e) A 50-liter fermentor is charged with 30 l of a sterile nutrient solution containing
0.5% cornsteep liquor
0.05% glucose monohydrate
0.3% "protein hydrolysate"
4 ml silicone SH
4 ml "Pluronic"
adjusted to pH 7.0
inoculated with 3 l of *Arthrobacter simplex* preliminary culture, and incubated under aeration (2 m$^3$ per hour) and agitation (220 rpm) for 9 hours at 30° C. The sterile solution of 11β,17α,21-trihydroxy-6α-methyl-4-pregnene-3,20-dione prepared in paragraph (c) and the additives described in paragraph (d) are then added to the culture. Fermentation is subsequently continued for 7 hours.

After fermentation has taken place, the culture broth, stabilized with 5 l of ethylene chloride, is extracted three times with respectively 20 l of ethylene chloride, and the ethylene chloride extract is concentrated under vacuum on a forced circulation evaporator at maximally 50° C. The product is thereafter purified by chromatography on aluminum oxide.

Yield: 19.1 g of 11β,17α,21-trihydroxy-6α-methyl-1,4-pregnadiene-3,20-dione, mp 235/236°–238° C.

EXAMPLE 8

(a) A 2-liter Erlenmeyer flask charged with 1 liter of a sterile nutrient solution containing
0.5% cornsteep liquor
0.05% glucose monohydrate
0.1% yeast extract
adjusted to pH 7.0
is inoculated with a supernatant broth of a dry culture of *Arthrobacter simplex* ATCC 6946 and shaken at 30° C. for 72 hours at 180 rpm.

(b) A 50-liter fermentor with 30 l of a sterile nutrient solution containing
0.5% cornsteep liquor
0.05% glucose monohydrate
0.1% yeast extract
4 ml silicone SH
4 ml "Pluronic"
adjusted to pH 7.0
is inoculated with 1 liter of *Arthrobacter simplex* incubation culture, and this preliminary culture is incubated at 30° C. under aeration (2 m$^3$ per hour) and agitation (220 rpm) for 24 hours.

(c) 3 g of 11β,21-dihydroxy-17α-propoxymethoxy-4-pregnene-3,20-dione is dissolved in 200 ml of ethylene glycol monomethyl ether and thereafter filtered under sterile conditions.

(d) 7.5 g CoSO$_4$.7H$_2$O and 7.5 g of (NH$_4$)$_2$SO$_4$ are dissolved in 500 ml of water, adjusted to pH 6.5, and sterilized.

(e) A 50-liter fermentor is charged with 30 l of a sterile nutrient solution containing
0.5% cornsteep liquor
0.05% glucose monohydrate
0.3% "protein hydrolysate"
4 ml silicone SH
4 ml "Pluronic"
adjusted to pH 7.0
inoculated with 3 l of *Arthrobacter simplex* preliminary culture, and incubated under aeration (2 m$^3$ per hour) and agitation (220 rpm) for 9 hours at 30° C. The sterile solution of 11β,21-dihydroxy-17α-propoxymethoxy-4-pregnene-3,20-dione as prepared in paragraph (c) and the additives disclosed in paragraph (d) are then added to the culture. Fermentation is thereafter continued for another 6 hours.

After fermentation has taken place, the culture broth, stabilized with 5 l of ethylene chloride, is extracted three times with respectively 20 l of ethylene chloride, and the ethylene chloride extract is concentrated under vacuum in a forced circulation evaporator at maximally 50° C. Then the product is purified by chromatography on aluminum oxide.

Yield: 2.4 g of 11β,21-dihydroxy-17α-propoxymethoxy-1,4-pregnadiene-3,20-dione, mp 121/125°–127° C.

EXAMPLE 9

(a) A 2-liter Erlenmeyer flask charged with 1 liter of a sterile nutrient solution containing
0.5% cornsteep liquor
0.05% glucose monohydrate
0.1% yeast extract
adjusted to pH 7.0
is inoculated with a supernatant broth of a dry culture of *Arthrobacter simplex* ATCC 6946 and shaken at 30° C. for 72 hours at 180 rpm.

(b) A 50-liter fermentor with 30 l of a sterile nutrient solution containing
0.5% cornsteep liquor
0.05% glucose monohydrate
0.1% yeast extract
4 ml silicone SH
4 ml "Pluronic"
adjusted to pH 7.0
is inoculated with 1 liter of *Arthrobacter simplex* incubation culture, and this preliminary culture is incubated at 30° C. under aeration (2 m$^3$ per hour) and agitation (220 rpm) for 24 hours.

(c) 7.5 g of 11β,21-dihydroxy-17α-isopropoxymethoxy-4-pregnene-3,20-dione is dissolved in 200 ml of ethylene glycol monomethyl ether and subsequently filtered under sterile conditions.

(d) 7.5 g of CoSO$_4$.7H$_2$O and 7.5 g of (NH$_4$)$_2$SO$_4$ are dissolved in 500 ml of water, adjusted to pH 6.5, and sterilized.

(e) A 50-liter fermentor is charged with 30 l of a sterile nutrient solution containing
0.5% cornsteep liquor
0.05% glucose monohydrate
0.3% "protein hydrolysate"
4 ml silicone SH
4 ml "Pluronic"
adjusted to pH 7.0 inoculated with 3 l of *Arthrobacter simplex* preliminary culture, and incubated under aeration (2 m³ per hour) and agitation (220 rpm) for 9 hours at 30° C. Then, the sterile solution of 11β,21-dihydroxy-17α-isopropoxymethoxy-4-pregnene-3,20-dione as prepared in paragraph (c) and the additives as described in paragraph (d) are added to the culture. Fermentation is thereafter continued for 12 hours.

After fermentation has been achieved, the culture broth, stabilized with 5 l of ethylene chloride, is extracted three times with respectively 20 l of ethylene chloride, and the ethylene chloride extract is concentrated under vacuum in a forced circulation evaporator at maximally 50° C. The product is then purified by chromatography on aluminum oxide.

Yield: 4.2 g of 11β,21-dihydroxy-17α-isopropoxymethoxy-1,4-pregnadiene-3,20-dione, mp 58/63°–65° C.

EXAMPLE 10

(a) A 2-liter Erlenmeyer flask charged with 1 liter of a sterile nutrient solution containing
0.5% cornsteep liquor
0.05% glucose monohydrate
0.1% yeast extract
adjusted to pH 7.0
is inoculated with a supernatant broth of a dry culture of *Arthrobacter simplex* ATCC 6946 and shaken at 30° C. for 72 hours at 180 rpm.

(b) A 50-liter fermentor with 30 l of a sterile nutrient solution containing
0.5% cornsteep liquor
0.05% glucose monohydrate
0.1% yeast extract
4 ml silicone SH
4 ml "Pluronic"
adjusted to pH 7.0
is inoculated with 1 liter of *Arthrobacter simplex* incubation culture, and this preliminary culture is incubated at 30° C. under aeration (2 m³ per hour) and agitation (220 rpm) for 24 hours.

(c) 9 g of 11β,21-dihydroxy-17α-methoxymethoxy-4-pregnene-3,20-dione is dissolved in 300 ml of dimethylformamide and then filtered under sterile conditions.

(d) 7.5 g of CoSO₄.7H₂O and 7.5 g of (NH₄)₂SO₄ are dissolved in 500 ml of water, adjusted to pH 6.5, and sterilized.

(e) A 50-liter fermentor is charged with 30 l of a sterile nutrient solution containing
0.5% cornsteep liquor
0.05% glucose monohydrate
0.3% "protein hydrolysate"
4 ml silicone SH
4 ml "Pluronic"
adjusted to pH 7.0
inoculated with 3 l of *Arthrobacter simplex* preliminary culture, and incubated under aeration (2 m³ per hour) and agitation (220 rpm) for 9 hours at 30° C. Then the sterile 11β,21-dihydroxy-17α-methoxymethoxy-4-pregnene-3,20-dione solution produced in paragraph (c) and the additives disclosed in paragraph (d) are added to the culture. Fermentation is then continued for 6 hours.

After fermentation has taken place, the culture broth, stabilized with 5 l of ethylene chloride, is extracted three times with respectively 20 l of ethylene chloride, and the ethylene chloride extract is concentrated under vacuum in a forced circulation evaporator at maximally 50° C. Thereafter the product is purified by chromatography on aluminum oxide.

Yield: 5.4 g of 11β,21-dihydroxy-17α-methoxymethoxy-1,4-pregnadiene-3,20-dione, mp 229/230°–231° C.

EXAMPLE 11

(a) A 2-liter Erlenmeyer flask charged with 1 liter of a sterile nutrient solution containing
0.5% cornsteep liquor
0.05% glucose monohydrate
0.1% yeast extract
adjusted to pH 7.0
is inoculated with a supernatant broth of a dry culture of *Arthrobacter simplex* ATCC 6946 and shaken at 30° C. for 72 hours at 180 rpm.

(b) A 50-liter fermentor with 30 l of a sterile nutrient solution containing
0.5% cornsteep liquor
0.05% glucose monohydrate
0.1% yeast extract
4 ml silicone SH
4 ml "Pluronic"
adjusted to pH 7.0
is inoculated with 1 liter of *Arthrobacter simplex* incubation culture, and this preliminary culture is incubated at 30° C. under aeration (2 m³ per hour) and agitation (220 rpm) for 24 hours.

(c) 7.5 g of 17β-hydroxy-17α-methyl-4-androsten-3-one is dissolved in 150 ml of dimethylformamide and then filtered under sterile conditions.

(d) 12 g of CoSO₄.7H₂O and 12 g of (NH₄)₂SO₄ are dissolved in 500 ml of water, adjusted to pH 6.5, and sterilized.

(e) A 50-liter fermentor is charged with 30 l of a sterile nutrient solution containing
0.5% cornsteep liquor
0.05% glucose monohydrate
0.3% "protein hydrolysate"
4 ml silicone SH
4 ml "Pluronic"
adjusted to pH 7.0
inoculated with 3 l of *Arthrobacter simplex* preliminary culture, and incubated under aeration (2 m³ per hour) and agitation (220 rpm) for 6 hours at 30° C. Thereafter, the sterile 17β-hydroxy-17α-methyl-4-androsten-3-one solution prepared in paragraph (c) and the additives described in paragraph (d) are added to the culture. Fermentation is then continued for 20 hours.

After fermentation has been completed, the culture broth, stabilized with 5 l of ethylene chloride, is extracted three times with respectively 20 l of ethylene chloride, and the ethylene chloride extract is concentrated under vacuum in a forced circulation evaporator at maximally 50° C. The product is thereafter purified by chromatography on aluminum oxide.

Yield: 6.2 g of 17β-hydroxy-17α-methyl-1,4-androstadien-3-one, mp 163°–164.5° C.

EXAMPLE 12

(a) A 2-liter Erlenmeyer flask charged with 1 liter of a sterile nutrient solution containing
0.5% cornsteep liquor
0.05% glucose monohydrate
0.1% yeast extract
adjusted to pH 7.0
is inoculated with a supernatant broth of a dry culture of *Arthrobacter simplex* ATCC 6946 and shaken at 30° C. for 72 hours at 180 rpm.

(b) A 50-liter fermentor with 30 l of a sterile nutrient solution containing
0.5% cornsteep liquor
0.05% glucose monohydrate
0.1% yeast extract
4 ml silicone SH
4 ml "Pluronic"
adjusted to pH 7.0
is inoculated with 1 liter of *Arthrobacter simplex* incubation culture, and this preliminary culture is incubated at 30° C. under aeration (2 m³ per hour) and agitation (220 rpm) for 24 hours.

(c) 6 g of 11α,17α-dihydroxy-16β-methyl-4-pregnene-3,20-dione is dissolved in 150 ml of ethylene glycol monomethyl ether and thereafter filtered under sterile conditions.

(d) 12 g of CoSO₄.7H₂O and 12 g of (NH₄)₂SO₄ are dissolved in 500 ml of water, adjusted to pH 6.5, and sterilized.

(e) A 50-liter fermentor is charged with 30 l of a sterile nutrient solution containing
0.5% cornsteep liquor
0.05% glucose monohydrate
0.3% "protein hydrolysate"
4 ml of silicone SH
4 ml of "Pluronic"
adjusted to pH 7.0
inoculated with 3 l of *Arthrobacter simplex* preliminary culture, and incubated under aeration (2 m³ per hour) and agitation (220 rpm) for 6 hours at 30° C. Then the sterile solution of 11α,17α-dihydroxy-16β-methyl-4-pregnene-3,20-dione described in paragraph (c) and the additives prepared in paragraph (d) are added to the culture. Fermentation is thereafter continued for 20 hours.

After fermentation has taken place, the culture broth, stabilized with 5 l of ethylene chloride, is extracted three times with respectively 20 l of ethylene chloride, and the ethylene chloride extract is concentrated under vacuum in a forced circulation evaporator at maximally 50° C. The product is then purified by chromatography on aluminum oxide.

Yield: 4.6 g of 11α,17α-dihydroxy-16β-methyl-1,4-pregnadiene-3,20-dione, mp 203/204°-205° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a 3-oxo-Δ¹,⁴-steroid of the formula

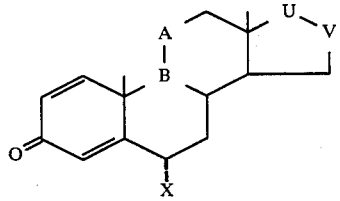

wherein X is hydrogen, chlorine, fluorine or methyl,

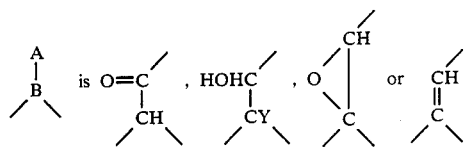

wherein Y is hydrogen, fluorine, or chlorine, and

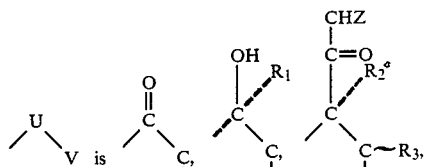

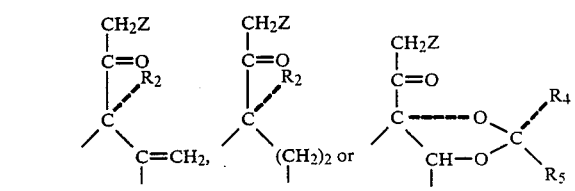

wherein
Z is hydrogen, hydroxy, fluorine, or chlorine,
R₁ is hydrogen or an alicyclic hydrocarbon residue of 1-4 carbon atoms,
R₂ is hydrogen, hydroxy, alkyl of 1-6 carbon atoms optionally interrupted by an oxygen atom or a sulfur atom, alkanoyloxy of 1-6 carbon atoms, or benzoyloxy,
R₃ is hydrogen, hydroxy or methyl, and
R₄ and R₅ each independently is alkyl or 1-4 carbon atoms, comprising
fermenting a corresponding 3-oxo-Δ⁴-steroid of the formula

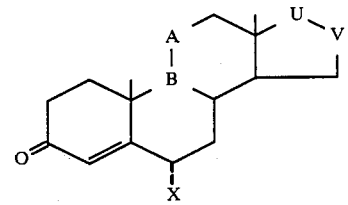

wherein X,

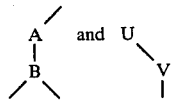

are as defined above, or a 21-ester thereof with an alkanecarboxylic acid of 1-6 carbon atoms, with a living culture of *Arthrobacter simplex* in the presence of 0.04 g to 0.12 g of cobalt(II) ions per liter of culture broth.

2. A process of claim 1 wherein the Co ions are provided by adding $CoCl_2$, $Co(NO_3)_2$, $CoSO_4$ or $CoSO_4 \cdot 7H_2O$ to the culture broth.

3. A process of claim 1 wherein the concentration of cobalt(II) ions is 0.04–0.08 g per liter of broth.

4. A process of claim 1 wherein the Co ions are provided by adding $CoSO_4 \cdot 7H_2O$ to the culture broth.

5. A process of claim 1, wherein the living culture of *Arthrobacter simplex* is of the strain ATCC 6946.

6. A process of claim 1, wherein the living culture of *Arthrobacter simplex* is of the strain IFO (3530) or ATCC 13 260.

* * * * *